(12) United States Patent
Selve

(10) Patent No.: US 7,875,652 B2
(45) Date of Patent: Jan. 25, 2011

(54) METHOD AND COMPOSITION FOR TREATING PAIN OR TINNITUS AUREUM

(75) Inventor: Norma Selve, Troisdorf (DE)

(73) Assignee: UCB Pharma GmbH, Monheim (DE)

( * ) Notice: Subject to any disclaimer, the term of this patent is extended or adjusted under 35 U.S.C. 154(b) by 835 days.

(21) Appl. No.: 10/466,295

(22) PCT Filed: Mar. 19, 2002

(86) PCT No.: PCT/EP02/03032

§ 371 (c)(1),
(2), (4) Date: Jul. 14, 2003

(87) PCT Pub. No.: WO02/074297

PCT Pub. Date: Sep. 26, 2002

(65) Prior Publication Data

US 2004/0220077 A1 Nov. 4, 2004

(30) Foreign Application Priority Data

Mar. 21, 2001 (EP) ................................. 01107026

(51) Int. Cl.
*A61K 31/16* (2006.01)
*A61K 31/165* (2006.01)
(52) U.S. Cl. ...................... 514/616; 514/617
(58) Field of Classification Search .................. 514/616, 514/617
See application file for complete search history.

(56) References Cited

U.S. PATENT DOCUMENTS

| | | | |
|---|---|---|---|
| 4,303,673 A | 12/1981 | Biedermann et al. ......... | 424/324 |
| 4,510,082 A | 4/1985 | Gesellchen et al. ... | 260/112.5 R |
| 4,513,009 A | 4/1985 | Roques et al. .............. | 514/513 |
| 4,533,657 A | 8/1985 | Morgan ....................... | 514/19 |
| 4,618,708 A | 10/1986 | Roques et al. .............. | 562/448 |
| 4,707,468 A | 11/1987 | Yoshino et al. .............. | 514/16 |
| 5,378,729 A | 1/1995 | Kohn et al. .............. | 514/231.2 |
| 5,508,266 A | 4/1996 | Fink ............................. | 514/19 |
| 5,536,853 A | 7/1996 | Spellmeyer et al. ......... | 549/441 |
| 5,585,358 A | 12/1996 | Bialer et al. .................. | 514/19 |
| 5,654,301 A | 8/1997 | Kohn et al. .............. | 514/231.2 |
| 5,656,267 A | 8/1997 | Sagen et al. ............. | 424/93.21 |
| 5,760,038 A | 6/1998 | Murugesan et al. ......... | 514/252 |
| 5,773,475 A | 6/1998 | Kohn .......................... | 514/616 |
| 5,780,589 A | 7/1998 | Lazarus et al. .............. | 530/331 |
| 5,885,999 A | 3/1999 | Elliott et al. ................ | 514/258 |
| 6,001,876 A | 12/1999 | Singh ......................... | 514/561 |
| 6,028,102 A | 2/2000 | Bialer et al. ................ | 514/489 |
| 6,037,324 A | 3/2000 | Schwender et al. ........... | 514/18 |
| 6,083,941 A | 7/2000 | Farb ............................ | 514/177 |
| 6,083,951 A | 7/2000 | Bradbury .................... | 514/256 |
| 6,103,732 A | 8/2000 | Amberg et al. .............. | 514/269 |
| 6,114,390 A | 9/2000 | Engel et al. ................. | 514/595 |
| 6,126,939 A | 10/2000 | Eisenbach-Schwartz et al. ....................... | 424/185.1 |
| 6,180,611 B1 | 1/2001 | Montana et al. ............... | 514/19 |
| 6,277,825 B1 | 8/2001 | Olivera et al. .................. | 514/13 |
| 6,737,408 B1 | 5/2004 | Balasubramanium et al. . | 514/18 |
| 6,803,481 B2 * | 10/2004 | Selve ......................... | 560/157 |
| 6,884,910 B2 * | 4/2005 | Harris ........................ | 562/553 |
| 2002/0052418 A1 | 5/2002 | Shirvan et al. .............. | 514/626 |
| 2003/0216466 A1 | 11/2003 | Scheuerman et al. ........ | 514/513 |
| 2004/0101582 A1 | 5/2004 | Wolicki ....................... | 424/760 |
| 2004/0204495 A1 | 10/2004 | Shirvan et al. .............. | 514/616 |
| 2005/0013856 A1 | 1/2005 | Trivedi et al. ............... | 424/464 |
| 2005/0043675 A1 | 2/2005 | Pastore et al. ................. | 604/67 |
| 2005/0209163 A1 | 9/2005 | Stoehr ......................... | 514/19 |
| 2005/0227961 A1 | 10/2005 | Kucharik et al. ....... | 514/211.13 |
| 2005/0261204 A1 | 11/2005 | Stoehr ......................... | 514/19 |
| 2005/0288234 A1 | 12/2005 | Stoehr ......................... | 514/19 |
| 2006/0009384 A1 | 1/2006 | Rudd et al. ................... | 514/12 |
| 2006/0046957 A1 | 3/2006 | Beyreuther et al. ........... | 514/7 |
| 2006/0100157 A1 | 5/2006 | Rauschkolb-Loffler et al. .......................... | 514/18 |
| 2006/0135437 A1 | 6/2006 | Stoehr et al. ................. | 514/19 |
| 2006/0252749 A1 | 11/2006 | Stohr ........................ | 514/220 |
| 2007/0042969 A1 | 2/2007 | Rauschkolb-Loffler et al. .......................... | 514/19 |
| 2007/0043120 A1 | 2/2007 | Beyreuther et al. ......... | 514/616 |
| 2007/0048372 A1 | 3/2007 | Beyreuther et al. ......... | 424/464 |
| 2007/0054962 A1 | 3/2007 | Selve ......................... | 514/575 |

(Continued)

FOREIGN PATENT DOCUMENTS

DE 195 33 023 4/1996

(Continued)

OTHER PUBLICATIONS

Hama et al. "NMDA-induced spinal hypersensitivity is reduced by naturally derived peptide analog[Ser']histogranin," Pharmacology Biochemistry and Behavior, 1999, vol. 62, No. 1, pp. 67-74.*

(Continued)

*Primary Examiner*—Shengjun Wang
(74) *Attorney, Agent, or Firm*—Harness, Dickey & Pierce, P.L.C.

(57) ABSTRACT

The present invention concerns the novel use of compounds of the Formula I: for treating allodynia as major and unique pain symptom independent of the nature of an underlying disease, but that is often related to neuropathic pain or other different types of chronic or phantom pain.

(I)

$$Ar-CH_2NHC(=O)-\underset{\underset{Q}{\overset{}{CH_2}}}{\overset{H}{\underset{|}{C}}}-\underset{}{\overset{H}{\underset{|}{N}}}-C(=O)-Q_1$$

10 Claims, No Drawings

U.S. PATENT DOCUMENTS

| | | | | |
|---|---|---|---|---|
| 2007/0197657 A1 | 8/2007 | Beyreuther et al. | ......... | 514/616 |
| 2008/0027137 A1 | 1/2008 | Riedner et al. | ............. | 514/561 |
| 2008/0287545 A1 | 11/2008 | Scheller et al. | ............ | 514/616 |
| 2009/0018197 A1 | 1/2009 | Rudd et al. | ................. | 514/563 |
| 2009/0018198 A1 | 1/2009 | Stohr | ........................ | 514/563 |

FOREIGN PATENT DOCUMENTS

| | | |
|---|---|---|
| EP | 0 555 537 | 8/1993 |
| EP | 0 997 147 | 5/2000 |
| EP | 1243263 A1 * | 9/2002 |
| EP | 1 243 263 | 11/2002 |
| EP | 1 486 205 | 12/2004 |
| EP | 1 486 206 | 12/2004 |
| EP | 1 537 862 | 6/2005 |
| EP | 1 541 138 | 6/2005 |
| EP | 1 579 858 | 9/2005 |
| EP | 1 688 137 | 8/2006 |
| WO | WO 92/14706 | 9/1992 |
| WO | WO 95/30645 | 11/1995 |
| WO | WO 96/11209 | 4/1996 |
| WO | WO 96/32100 | 10/1996 |
| WO | WO 9632100 A1 * | 10/1996 |
| WO | WO 97/38980 | 10/1997 |
| WO | WO 97/38981 | 10/1997 |
| WO | WO 98/09953 | 3/1998 |
| WO | WO 99/02146 | 1/1999 |
| WO | WO 99/07413 | 2/1999 |
| WO | WO 99/16444 | 4/1999 |
| WO | WO 99/23078 | 5/1999 |
| WO | WO 99/43309 | 9/1999 |
| WO | WO 99/56761 | 11/1999 |
| WO | WO 9965903 A1 * | 12/1999 |
| WO | WO 00/51586 | 9/2000 |
| WO | WO 01/17976 | 3/2001 |
| WO | WO 01/78762 | 10/2001 |
| WO | WO 02/13766 | 2/2002 |
| WO | WO 02/15922 A2 | 2/2002 |
| WO | WO 02/42256 | 5/2002 |
| WO | WO 02/074297 | 9/2002 |
| WO | WO 02/074784 | 9/2002 |
| WO | WO 02/076979 | 10/2002 |
| WO | WO 02/087548 | 11/2002 |
| WO | WO 02/088664 | 11/2002 |
| WO | WO 03/000642 | 1/2003 |
| WO | WO 2004/014895 | 2/2004 |
| WO | WO 2004/043926 | 5/2004 |
| WO | WO 2004/046178 | 6/2004 |
| WO | WO 2004/060353 | 7/2004 |
| WO | WO 2004/066987 | 8/2004 |
| WO | WO 2004/066990 | 8/2004 |
| WO | WO 2004/091585 | 10/2004 |
| WO | WO 2004/100871 | 11/2004 |
| WO | WO 2005/053667 | 6/2005 |
| WO | WO 2005/092313 | 10/2005 |
| WO | WO 2005/099740 | 10/2005 |
| WO | WO 2005/120539 | 12/2005 |

OTHER PUBLICATIONS

Definition of allodynia, http://www.medterms.com/script/ain/art.asp?articlekey=25197.*
Definition of allodynia, http://www.medterms.com/script/ain/art.asp?articlekey=25197, 2006.*
Abbott et al. (1995) Pain 60:91-102.
Abdulla & Smith (2002) J. Neurophysiol. 88:2518-2529.
Akiba et al. (2003) Receptors & Channels 9:291-299.
Amir et al. (2006) J. Pain 7(5 Suppl. 3):S1-S29.
Arnér & Meyerson (1988) Pain 33:11-23.
Arnt et al. (1984) Pol. J. Pharmacol. Pharm. 36:221-230.
Arroyo (2003) "Safety of SPM 927 in subjects with epilepsy and neuropathic pain" Poster presented at AES Scientific Exhibit, Dec. 5-10, 2003.
Backonja (2002) Neurology 59:S14-S17.
Backonja (2003) Anesth. Analg. 97:785-790.
Béguin et al. (2003) Bioorganic & Medicinal Chemistry 11:4275-4285.
Béguin et al. (2004) Bioorganic & Medicinal Chemistry 12:3079-3096.
Ben-Menachem (2005) "A dose-response, placebo-controlled trial using lacosamide as adjunctive therapy in subjects with partial seizures" Presented at 26th International Epilepsy Congress, Paris, Aug. 28-Sep. 1, 2005.
Ben-Menachem et al. (2005) "Efficacy and safety of adjunctive oral lacosamide for the treatment of partial-onset seizures in patients with epilepsy" Poster P03.101 presented at American Academy of Neurology 57th Annual Meeting, Miami Beach, FL.
Bennett & Xie (1988) Pain 33(1):87-107 (abstract only http://www.ncbi.nlm.nih.gov/pubmed/2837713).
Bennett et al. (2000) Pain 86:163-175.
Beyak et al. (2004) Am. J. Physiol. Gastrointest. Liver Physiol. 287:G845-G855.
Beyreuther (2004) "Pharmacology of SPM 927 and its relevance to clinical practice for neuropathic pain" Presented at Visiongain Pain Management, 2004.
Beyreuther et al. (2004) "SPM 927 displays potent antinococeptive effects in rat models for inflammatory and neuropathic pain" Poster presented at Neuropathic Pain, May 13-14, 2004.
Beyreuther et al. (2006) "Effects of lacosamide as compared to other analgesics: a responder analysis in the streptozotocin rat model for diabetic neuropathic pain" Poster 618 presented at American Pain Society, 2006 (abstract at http://www.ampainsoc.org/db2/abstract/view?poster id=2637#618).
Beyreuther et al. (2006) "Lacosamide displays antinociceptive effects in a rat model for musculoskeletal pain induced by TNF" Poster 625 presented at American Pain Society, 2006 (abstract at http://www.ampainsoc.org/db2/abstract/view?poster_id=2643#625).
Beyreuther et al. (2006) "Lacosamide displays antinociceptive effects in rat models for arthritis pain" Poster 626 presented at American Pain Society, 2006 (abstract at http://www.ampainsoc.org/db2/abstract/view?poster_id=2644#626).
Beyreuther et al. (2006) Eur. J. Pharmacol. 539:64-70.
Beyreuther et al. (2007) CNS Drug Rev. 13(1):21-42.
Beyreuther et al. (2007) Arthritis Res. Therapy 9:R14, http://arthritis-research.com/content/9/1/R14.
Bialer et al. (2001) Epilepsy Res. 43:11-58.
Bialer et al. (2002) Epilepsy Res. 51:31-71.
Bilsky et al. (2000) J. Med. Chem. 43:2586-2590.
Biton et al. (2003) Epilepsia 44(Suppl. 9):259, abst. 2.241 (poster attached).
Biton et al. (2004) "Safety and tolerability of intravenous lacosamide as replacement for oral lacosamide in subjects with partial seizures" Poster presented at AES Scientific Exhibit, Dec. 3-7, 2004.
Biton et al. (2005) "Safety, tolerability and pharmacokinetics of intravenous lacosamide as replacement for oral lacosamide in subjects with partial seizures" Poster P02.148 presented at International Epilepsy Congress, Aug. 28-Sep. 1, 2005.
Biton (2006) "Multicenter, double-blind, double-dummy trial investigating safety, tolerability and pharmacokinetics of intravenous lacosamide (SPM 927) in subjects with partial seizures" Presented at European Congress on Epileptology 2006.
Blackburn-Munro et al. (2002) Eur. J. Pharmacol. 445:231-238.
Blair & Bean (2002) J. Neurosci. 22(23):10277-10290.
Blair & Bean (2003) J. Neurosci. 23(32):10338-10350.
Bretschneider et al. (2006) http://www.ampainsoc.org/db2/abstract/view?poster_id=2765#766.
Brodie (1996) Can. J. Neurol. Sci. 23(Suppl. 2):S6-S9.
Bunney & Garland (1982) Pharmacopsychiat. 15:111-115.
Caliendo et al. (2005) Curr. Med. Chem. 12(15):1721-1753.
Calvino et al. (1987) Behavioural Brain Res. 24:11-29.
Casey et al. (2003) Neuropsychopharmacol. 28:182-192.

Cawello et al. (2003) Epilepsia 44(Suppl. 9):95, abst. 1.265 (poster attached).
Cawello et al. (2004) Epilepsia 45(Suppl. 7):307, abst. 2.342 (poster attached).
Chevrier et al. (2004) Br. J. Pharmacol. 142:576-584.
Christensen et al. (1996) Pain 68:97-107.
Citrome (2003) Psychopharmacol. Bull. 37(Suppl. 2):74-88.
Colpaert et al. (1982) Life Sciences 31:67-75.
Cummins et al. (2004) J. Neurosci. 24(38):8232-8236.
Daniels et al. (2005) "Long-term safety and efficacy of lacosamide as adjunctive therapy in subjects with partial seizures: 96-week follow-up" Poster presented at AES Scientific Exhibit, Dec. 2-5, 2005.
Decosterd & Woolf (2000) Pain 87:149-158.
Doty et al. (2004) in Bialer et al., Epilepsy Res. 61:1-48, pp. 14-16.
Doty et al. (2004) "Update on the clinical development of SPM 927 (formerly harkoseride)" Presented at EILAT VII, May 2004.
Dowdall et al. (2004) Pharmacol. Biochem. Behavior 80:93-108.
Dubuisson & Dennis (1977) Pain 4:161-174.
Duncan & Kohn (2005) Epilepsy Res. 67:81-87.
Eller et al. (2005) Neurosurg. Focus 18(5):E3, 3 pp.
Elliott (1997) Brain Res. 754:221-226.
Erichsen & Blackburn-Munro (2002) Pain 98:151-161.
Errington et al. (2005) "Lacosamide has a unique molecular mode of action" Poster presented at AES Scientific Exhibit, Dec. 2-5, 2005.
Everill et al. (2001) Neurosci. 106(1):161-169.
Field et al. (1997) Br. J. Pharmacol. 121:1513-1522.
Field et al. (2002) J. Pharmacol. Exp. Ther. 303(2):730-735.
Fountain et al. (2000) Epilepsia 41(Suppl. 7):169 (presentation attached).
Freynhagen et al. (2005) Pain 115:254-263.
Grippo et al. (2005) Psychopharmacol. 179:769-780.
Han et al. (2000) Pain 84:253-261.
Hao et al. (2004) "SPM 927, a new anti-epileptic drug, alleviates neuropathic pain-like behaviors in rats after spinal cord or trigeminal nerve injury" Poster presented at Neuropathic Pain—Changing Paradigms in Diagnosis and Treatment, Madrid, May 2004.
Heers et al. (2006) "The preclinical profile of the novel anticonvulsant lacosamide" Poster presented at European Congress on Epileptology 2006.
Henriksson (1999) Bailliére's Clin. Rheumatol. 13(3):455-461.
Hidvegi et al. (2006) "Lacosamide in subjects with painful distal diabetic neuropathy: results of a multi-center, open-label, follow-on trial" Poster presented at American Pain Society, May 3-6, 2006.
Hofmann et al. (2003) Eur. J. Pharmacol. 470:17-25.
Holmberg et al. (2004) J. Med. Chem. 47:3927-3930.
Hong et al. (2004) J. Biol. Chem. 279(28):29341-29350.
Honore et al. (2000) Neurosci. 98(3):585-598.
Horstmann et al. (2002) Epilepsia 43(Suppl. 7):188, abst. 2.174 (poster attached).
Horstmann et al. (2003) Epilepsia 44(Suppl. 9):97, Abst. 1.271 (poster attached).
Horstmann et al. (2003) "SPM 927 does not prolong the QTc interval" Poster presented at 6th International Conference on the Mechanisms and Treatment of Neuropathic Pain, San Francisco, Sep. 18-20, 2003.
Hovinga (2003) IDrugs 6(5):479-485.
Hunskaar et al. (1985) J. Neurosci. Methods 14:69-76.
Hunt (2003) Clin. Orthopaedics Rel. Res. 409:96-105.
Hurley et al. (2002) Anesthesiology 97:1263-1273.
Ilyin et al. (2005) Br. J. Pharmacol. 144:801-812.
Jain (2000) Emerging Drugs 5(2):241-257.
Kelso (2005) Curr. Pharm. Design 11:3005-3011.
Kenney et al. (2006) http://www.ampainsoc.org/db2/abstract/view?poster id=2773#774.
Kim & Chung (1992) Pain 50(3):355-363.
Kropeit et al. (2004) Epilepsia 45(Suppl. 7): 123, abst. 1.323 (poster attached).
Kropeit et al. (2005) "Low drug-interaction potential of Lacosamide" Poster 702 presented at American Pain Society 2005 (abstract at http://www.ampainsoc.org/db2/abstract/view?poster id=2394#702).
Kropeit et al. (2006) "Lacosamide has low potential for drug-drug-interaction" Poster 851 presented at American Pain Society 2006 (abstract at http://www.ampainsoc.org/db2/abstract/view?poster id=2848#851).
Lai et al. (2003) Curr. Opin. Neurobiol. 13:291-297.
Lai et al. (2004) Ann. Rev. Pharmacol. Toxicol. 44:371-397.
Lampert et al. (2006) Exp. Brain Res. 174(4):660-666.
Lawand et al. (1997) Eur. J. Pharmacol. 324:169-177.
Lee et al. (2000) NeuroReport 11(4):657-661.
Lee & Jeong (2002) J. Korean Med. Sci. 17:81-85.
Lesser et al. (2004) Neurology 63:2104-2110.
LeTiran et al. (2002) J. Med. Chem. 45:4762-4773.
Lu & Westlund (1999) J. Pharmacol. Exp. Ther. 290:214-219.
Lynch et al. (2004) Pain 110:56-63.
Mach et al. (2002) Neurosci. 113(1):155-166.
Macres (2000) "Understanding neuropathic pain" http://www.spineuniverse.com/displayarticle.php/article1614.html.
Maier et al. (2004) "A pilot randomized, double-blind, placebo-controlled pilot trial to investigate safety and efficacy of SPM 927 in subjects with postherpetic neuralgia" Poster presented at Neuropathic Pain, May 13-14, 2004.
Majumdar et al. (2004) Eur. J. Neurosci. 20:127-143.
McCleane (2003) CNS Drugs 17(14):1031-1043.
McCleane et al. (2003) Neurosci. Lett. 352:117-120.
Mohapatra et al. (2003) Mol. Cell. Neurosci. 23:314-324.
Moller (2000) J. Am. Acad. Audiol. 11(3):115-124.
Morrow et al. (2001) Soc. Neurosci. Conf. Abst. 508.
Morrow et al. (2003) "The effects of lacosamide in animal models for acute, inflammatory and neuropathic pain" Poster presented at AES Scientific Exhibit, Dec. 5-10, 2003.
Nakata et al. (2003) Biol. Psychiatry 53:571-576.
Patel et al. (2001) Pain 90:217-226.
Pessoa-Mahana et al. (2003) Mini Rev. Med. Chem. 3:77-93.
Priestley (2004) Curr. Drug Targets—CNS & Neurol. Disorders 3:441-456.
Randall & Selitto (1957) Arch. Int. Pharmacodyn. 91:409-419.
Rauck et al. (2003) "A randomized, double-blind, placebo-controlled trial to investigate the safety and efficacy of SPM 927 in painful diabetic neuropathy" Poster presented at 6th Int. Conf. on Mechanisms and Treatment of Neuropathic Pain, Sep. 2003.
Rauck et al. (2007) Clin. J. Pain 23(2):150-158.
Rauschkolb et al. (2004) "SPM 927, a novel promising pain treatment" Presented at Visiongain Pain Management, 2004.
Remy et al. (2004) Neuropharmacol. 47:1102-1112.
Richeimer (2000) "The Richeimer Pain Update" http:/www.helpforpain.com/arch2000dec.htm.
Rodger (1991) Can. Med. Assoc. J. 145:1571-1581.
Rosenfeld et al. (2003) Epilepsia 44(Suppl. 9):262, abst. 2.249 (poster attached).
Rosenfeld et al. (2005) Epilepsia 46(Suppl. 8):184, abst. 2.278 (poster attached).
Rosenstock et al. (2004) Pain 110:628-638.
Rüttiger et al. (2003) Hear. Res. 180:39-50.
Sachdeo et al. (2003) "An open-label, maximum tolerated dose trial to evaluate oral SPM 927 as adjunctive therapy in patients with partial seizures" Poster presented at 55th Annual Meeting, American Academy of Neurology, Mar. 2003.
Saddi & Abbott (2000) Pain 89:53-63.
Schiltmeyer et al. (2004) Epilepsia 45(Suppl. 7):313, abst. 2.361 (poster attached).
Schiltmeyer et al. (2006) "No interaction between lacosamide and metformin" Poster 850 presented at American Pain Society 2006 (abstract at http://www.ampainsoc.org/db2/abstract/view?poster_id=2847#850.
Seltzer et al. (2001) Pain 93:101-106.
Shaibani et al. (2005) "An open-label follow-on trial to assess the long-term safety and efficacy of oral lacosamide in subjects with diabetic neuropathy" Poster presented at World Congress on Pain, Aug. 21-26, 2005.
Shiro et al. (1996) Psychiatry Clin. Neurosci. 50:141-146.
Silver & Soderlund (2005) Neurotoxicol. 26:397-406.
Sindrup & Jensen (1999) Pain 83:389-400.

Sommerville (2003) "Schwarz Pharma's Neurology Pipeline" http://www.schwarzpharma.com/_uploads/assets/1369_4_neurology_KNS_190203.pdf.
Sommerville & Whitesides (2004) "Intravenous SPM 927 (formerly harkoseride)" Presented at EILAT VII, May 2004.
Stein et al. (1988) Pharmacol. Biochem. Behavior 31:445-451.
Stoehr et al. (2005) "Lacosamide displays potent antinociceptive effects in animal models for neuropathic and inflammatory pain" Poster presented at World Congress on Pain, Aug. 21-26, 2005.
Stoehr & Beyreuther (2005) "The effect of lacosamide in comparison to other analgesics in rat models for neuropathic pain" Poster presented at 8th Int. Conf. on Mechanisms and Treatment of Neuropathic Pain, San Francisco, Nov. 3-5, 2005.
Stoehr et al. (2006) Eur. J. Pain 10:241-249.
Teng & Abbott (1998) Pain 76:337-347.
Tjølsen (1992) Pain 51:5-17.
Tjølsen & Hole (1997) in Dickinson & Besson, ed., "The Pharmacology of Pain", chap. 1, pp. 1-20; Berlin: Springer-Verlag.
Vaiciene et al. (2006) "Multicenter, open-label trial investigating safety and tolerability of intravenous lacosamide (SPM 927) as replacement for oral lacosamide in subjects with partial seizures: report of first cohort" Poster presented at European Congress on Epileptology 2006.
Vos et al. (1994) J. Neurosci. 14(5):2708-2723.
Watson et al. (1997) Pain 70:53-58.
Wheeler-Aceto & Cowan (1991) Psychopharmacol. 104:35-44.
Whitesides et al. (2004) "Long-term safety and efficacy of lacosamide as adjunctive therapy in subjects with partial seizures: 48-week follow-up" Poster presented at AES Scientific Exhibit, Dec. 3-7, 2004.
Wood et al. (2002) in "Sodium Channels and Neuronal Hyperexcitability", pp. 159-172; Chichester: Wiley.
Wood et al. (2004) J. Neurobiol. 61:55-71.
Wymer et al. (2005) "A multi-center, randomized double-blind, placebo-controlled trial to assess the efficacy and safety of lacosamide in subjects with painful distal diabetic neuropathy." 8th Int. Conf. on Mechanisms and Treatment of Neuropathic Pain, San Francisco, Nov. 3-5, 2005.
Xu et al. (1992) Pain 48(2):279-290 (abstract only).
Yezierski et al. (1998) Pain 75:141-155.
Ziegler et al. (2005) "Efficacy and safety of lacosamide in the treatment of neuropathic pain attributed to distal diabetic neuropathy." 8th Int. Conf. on Mechanisms and Treatment of Neuropathic Pain, San Francisco, Nov. 3-5, 2005.
Fisher, at al. (2003) "Trigeminal Neuralgia: current treatments and future developments." Expert Opin. Emerging Drugs 8(1):123-143.
Gerke, et al. (2003) "Thalamic neuronal activity in rats with mechanical allodynia following contusive spinal cord injury," Neuroscience 117:715-722.
Hovinga (2002) "Novel anticonvulsant medications in development." Expert Opin. Investig. Drugs 11(10) 1387-1405.
Office Action, dated Sep. 21, 2006 issued in U.S. Appl. No. 11/145,965.
Office Action, dated May 29, 2008 issued in U.S. Appl. No. 11/145,965.
Office Action, dated Sep. 11, 2007 issued in U.S. Appl. No. 11/507,110.
Office Action, dated Jul. 10, 2008 issued in U.S. Appl. No. 11/507,110.
Office Action, dated Feb. 3, 2010 issued in U.S. Appl. No. 11/507,110.
Office Action, dated Apr. 17, 2009 issued in U.S. Appl. No. 11/507,110.
Office Action, dated Sep. 11, 2006 issued in U.S. Appl. No. 11/149,181.
Office Action, dated Feb. 5, 2007 issued in U.S. Appl. No. 11/149,181.
Office Action, dated Oct. 6, 2008 issued in U.S. Appl. No. 11/506,578.
Office Action, dated Dec. 27, 2007 issued in U.S. Appl. No. 11/506,578.
Office Action, dated Apr. 29, 2009 issued in U.S. Appl. No. 11/506,578.
Office Action, dated Oct. 29, 2008 issued in U.S. Appl. No. 11/506,577.
Office Action, dated May 12, 2009 issued in U.S. Appl. No. 11/506,577.
Office Action, dated Dec. 17, 2009 issued in U.S. Appl. No. 11/506,577.
Office Action, dated Oct. 29, 2007 issued in U.S. Appl. No. 11/342,140.
Office Action, dated Oct. 21, 2009 issued in U.S. Appl. No. 11/342,140.
Office Action, dated Mar. 31, 2009 issued in U.S. Appl. No. 11/342,140.
Office Action, dated Aug. 20, 2008 issued in U.S. Appl. No. 11/342,140.
Office Action, dated Oct. 20, 2006 issued in U.S. Appl. No. 11/000,951.
Office Action, dated Jan. 22, 2009 issued in U.S. Appl. No. 11/000,951.
Office Action, dated Dec. 11, 2007 issued in U.S. Appl. No. 11/000,951.
Office Action, dated Aug. 19, 2009 issued in U.S. Appl. No. 11/000,951.
Office Action, dated Oct. 2, 2006 issued in U.S. Appl. No. 11/148,429.
Office Action, dated Jul. 28, 2008 issued in U.S. Appl. No. 11/148,429.
Office Action, dated Dec. 7, 2007 issued in U.S. Appl. No. 11/148,429.
Office Action, dated Dec. 17, 2009 issued in U.S. Appl. No. 11/148,429.
Office Action, dated Oct. 16, 2007 issued in U.S. Appl. No. 11/129,376.
Office Action, dated Mar. 5, 2007 issued in U.S. Appl. No. 11/129,376.
Office Action, dated Nov. 28, 2006 issued in U.S. Appl. No. 11/002,414.
Office Action, dated Mar. 2, 2010 issued in U.S. Appl. No. 10/599,976.
Office Action, dated Feb. 11, 2004 issued in U.S. Appl. No. 10/344,885.
Office Action, dated Dec. 28, 2006 issued in U.S. Appl. No. 11/089,441.
Office Action, dated Dec. 27, 2007 issued in U.S. Appl. No. 11/506,523.
Office Action, dated Apr. 15, 2010 issued in U.S. Appl. No. 12/188,419.
T. S. Jensen, *European Journal of Neurology*, vol. 7, Sup.7, pp. 3-4 (2000).
A. Lockwood et al., Website Document, "Tinnitus", 9 pages, 2003.

* cited by examiner

METHOD AND COMPOSITION FOR TREATING PAIN OR TINNITUS AUREUM

This application is a U.S. national stage filing under 35 U.S.C. §371 of International Application No. PCT/EP2002/03032 filed on Mar. 19, 2002, which claims priority of European Application No. EP 01107026.5 filed on Mar. 21, 2001. The disclosure of each of the applications identified in this paragraph is incorporated herein by reference in its entirety.

BACKGROUND OF THE INVENTION

The present invention relates to the novel use of a group of specific amino acid derivatives according to Formula I for the preparation of pharmaceutical compositions useful for the treatment of allodynia as a major and unique pain symptom independent of the nature of an underlying disease, but that is often related to neuropathic pain or other different types of chronic or phantom pain. Particularly the present invention relates to the novel use of harkoseride and its derivatives for the preparation of pharmaceutical compositions useful for the treatment of allodynia as a major and unique pain symptom independent of the nature of an underlying disease, but that is often related to neuropathic pain, or other different types of chronic or phantom pain.

The chemical name of SPM 927 which is also hereinafter referred to as harkoseride is (R)-2-Acetamido-N-benzyl-3-methoxypropionamide.

The compounds of the invention are known agents useful in antiseizure therapy for central nervous system disorders such as epilepsy, stroke and cerebral ischemia.

The instant invention concerns the novel use of a compound of Formula I below for the preparation of pharmaceutical compositions useful for the treatment of pain, particularly for the treatment of chronic pain disorders and especially for the treatment of allodynia as a major and unique pain symptom independent of the nature of an underlying disease, but that is often related to neuropathic pain conditions, or other different types of chronic or phantom pain and tinnitus aureum.

According to the invention compounds are those of Formula I

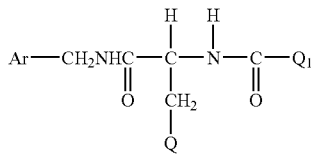

(Formula I)

or a pharmaceutically acceptable salt thereof wherein
Ar is phenyl which is unsubstituted or substituted with at least one halo group;
Q is lower alkoxy containing 1-3 carbon atoms and $Q_1$ is methyl;
diastereomers and enantiomers of compounds of Formula I are Included in the invention.

Preferred compounds of the invention are those according to Formula I in which the compounds are an (R), (S), or (R,S) isomer.

The most preferred compound of the invention is (R)-2-Acetamido-N-benzyl-3-methoxypropionamide or its pharmaceutically acceptable salt thereof.

Pain is a subjective experience and the perception of pain is performed in particular parts of the Central Nervous System (CNS).

Usually noxious (peripheral) stimuli are transmitted to the Central Nervous System beforehand, but pain is not always associated with nociception.

A broad variety of different types of clinical pain exists, that are derived from different underlying pathophysiological mechanisms and that will need different treatment approaches.

The perception of pain may be characterized by three major types of clinical pain:
- acute pain
- chronic pain
- neuropathic pain Acute clinical pain typically results from inflammation or soft tissue injury. This type of pain is adaptive and has the biologically relevant function of warning and enabling healing and repair of an already damaged body part to occur undisturbed. A protective function is achieved by making the injured/inflamed area and surrounding tissue hypersensitive to all stimuli so that contact with any external stimulus is avoided. The neuronal mechanisms underlying this type of clinical pain are fairly well understood and pharmacological control of acute clinical pain is available and effective by means of e.g. Non-Steroidal Anti-Inflammatory Drugs (NSAIDs) up to opioids depending on type and extension of the sensation.

Chronic clinical pain appears as sustained sensory abnormalities resulting from an ongoing peripheral pathology such as cancer of chronic inflammation (e.g. arthritis) or it can be independent of the initiating triggers. The latter being maladaptive, offering no survival advantage and very often no effective treatment is available.

Neuropathic pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Neuropathic pain shows two different pathophysiological mechanisms which have to be considered:

First, enhanced activity of afferent nociceptive neurons following sensitisation of (sleeping) neurons (e.g., inflammatory pain, cancer pain, headache, lower back pain, visceral pain, migraine) with the primary afferent nociceptive neuron remaining intact, though the receptor activity is changed and reduced thresholds, increase of firing rates and starting of or increase of spontaneous activity are typically found.

Second, ectopic activity of afferent nociceptive neurons following lesions of its axons (e.g., peripheral and central neuropathic pain), with the primary afferent neuron being damaged. This leads to irreversible peripheral and central biochemical, morphological and functional changes. Therefore, (peripheral) neuropathy is broadly defined as a disease of the (peripheral) nervous system.

There are several causes of human neuropathy with considerable variability in symptoms and neurological deficits. Painful neuropathies are defined as neurological disorders characterised by persistence of pain and hypersensitivity in a body region, of which the sensory innervation has been damaged, but damage to sensory nerves does not always produce neuropathic pain, usually loss of sensation rather than hypersensitivity or pain are observed.

Specific somatosensory disorders are referred to as allodynia (innocuous somatosensory stimulation evokes abnormal intense pain sensation with an explosive, radiating character often outlasting stimulus duration like a trigger), hyperalgesia (noxious stimulation evokes more intense and prolonged pain sensations), paresthesia (spontaneous aversive but nonpainful sensations, described as tingling or "pins and needles"), dysesthesia (evoked as well as spontaneous abnormal sensations).

Several key events are agreed in as common pathophysiological events of abnormal pain states particularely following peripheral nerve injury. Thus, high frequency spontaneous discharge from ectopic site is followed by an increased responsiveness of dorsal horn neurons and expansion of the receptive field, often defined as central sensitisation.

Common analgesics like opioids and non-steroidal anti-inflammatory drugs (NSAIDs) improve only insufficiently chronic abnormal pain syndromes. In the search for alternative treatment regimes to produce satisfactory and sustained pain relief, corticosteroids, conduction blockade, glycerol, antidepressants, local anesthetics, gangliosids and electro-stimulation have been tried, but mainly anti-convulsants have been found useful against various types of neuropathic pain conditions, but appear to be most effective in cases of paroxysmal, lancinating events, e.g. trigeminal neuralgia.

If general overactivity and unleaded low threshold activation of sensory neurons is considered as one of the main syndromes of neuropathy and neuropathic pain sensation with a marked mechanoallodynia as the most disabling clinical sympton, selective inhibition of this pathophysiological event instead of general inhibition of high threshold noxious stimuli (by e.g. local anesthetics) of the normal sensory nociception provides clear advantages.

The conditions listed above are known to be poorly treated by currently marketed analgesics such as opioids or nonsteroidal anti-inflammatory drugs (NSAID's) due to insufficient efficacy or limiting side effects.

It is an object of this invention to provide a novel use of compounds according to the aforementioned Formula I and its derivatives for the preparation of pharmaceutical compositions useful for the treatment of allodynia as a major and unique pain symptom Independent of the nature of an underlying disease, but that is often related to neuropathic pain, or other different types of chronic or phantom pain.

Particularly it is an object of this invention to provide a novel use of harkoseride for the preparation of pharmaceutical compositions useful for the treatment of allodynia as a major and unique pain symptom independent of the nature of an underlying disease, but that is often related to neuropathic pain, or other different types of chronic or phantom pain.

Harkoseride, which chemical name is (R)-2-Acetamido-N-benzyl-3-methoxypropion-amide is one derivative selected of the group of specific amino acid derivatives.

This group of substances is disclosed in U.S. Pat. No. 5,378,729; U.S. Pat. No. 5,654,301 and 5,773,475. They show activity for the treatment of epilepsy and stroke. But there is no disclosure in the above references to make obvious the present invention.

The compounds of the present invention may form pharmaceutically acceptable salts with both organic and inorganic acids or bases.

For example, the acid addition salts of the basic compounds are prepared either by dissolving the free base in aqueous or aqueous alcohol solution or other suitable solvents containing the appropriate acid and isolating the salt by evaporating the solution.

Examples of pharmaceutically acceptable salts are hydrochlorides, hydrobromides, hydrosulfates, etc. as well as sodium, potassium, and magnesium, etc. salts.

The compounds of the present invention can contain one or several assymmetric carbon atoms. The invention includes the individual diastereomers or enantiomers, and the mixtures thereof. The individual diastereomers or enantiomers may be prepared or isolated by methods already well-knwon in the art.

According to the invention it is preferred that the compounds are in the (R)-configuration. It is preferred that the compounds are substantially enantiopure. Most preferred is the compound (R)-2-Acetamido-N-benzyl-3-methoxypropionamide.

The compounds of this invention may be synthesized as disclosed in the documents U.S. Pat. No. 5,378,729; U.S. Pat. No. 5,654,301 and U.S. Pat. No. 5,773,475.

The compounds made by the synthetic methods can be used as pharmaceutical compositions as agent in the treatment of pain when an effective amount of a compound of the Formula I, together with a pharmaceutically acceptable carrier is used. The pharmaceutical can be used in a method for treating such disorders in mammals, including human, suffering therefrom by administering to such mammals an effective amount of the compounds described above in unit dosage form.

The pharmaceutical compound, made in accordance with the present invention, can be prepared and administered in a wide variety of dosage forms by either oral or parenteral routes of administration. For example, these pharmaceutical compositions can be made in inert, pharmaceutically acceptable carriers which are either solid or liquid. Solid form preparations include powders, tablets, dispersible granules, capsules, cachets, and suppositories. Other solid and liquid form preparations could be made in accordance with known methods of the art and administered by the oral route in an appropriate formulation, or by a parenteral route such as intravenous, intramuscular, or subcutaneous injection as a liquid formulation.

The quantity of active compound in a unit dose of preparation may be varied or adjusted from about 1 mg to about 2×300 mg per day per patient. A daily dose range of about 1 mg to about 300 mg is preferred. The dosages, however, may be varied depending upon the requirement with a patient, the severity of the condition being treated, and the compound being employed. Determination of the proper dosage for particular situations is within the skill of the art.

The following working examples selected from specific animal models show the anti-neuropathic pain activity of harkoseride and its derivatives in general and the antiallodynia efficay of harkoseride and its derivatives in particular.

EXAMPLE 1

Formalin Test, Rat

Significant and dose dependent efficacy of harkoseride could be demonstrated in the late phase of the rat formalin test.

The formalin test is a chemically-induced tonic pain model in which biphasic changes of nociceptive behaviour are assessed and spinal/supraspinal plasticity of nociception is considered as a molecular basis for neuropathic pain particularly during the second (=late) phase of the test, during which most clinically used drugs against neuropathic pain are active. These features have resulted in the formalin test being accepted as a valid model of persistent clinical pain.

The compound was tested for anti-nociceptive properties by use of the weighted behavioural scoring method: Freely moving animals underwent observational assessment of the position of the left hind paw according to a rating score scaled 0-3 before and 10, 20, 30 and 40 min after injection of 0.05 ml of sterile 2.5% formalin under the skin on the dorsal surface of the paw. Harkoseride, administered i.p. just prior to formalin injection produced dose dependant reduction of the formalin-induced tonic inflammatory nociceptive behaviour as shown in table 1 (weighted pain scores±SEM, n=11-12/group).

TABLE 1

Weighted pain score, formalin test, rat

| Dose [mg/kg] | No. of Animals | BASELINE | Time After Injection of formalin and SPM 927 | | | |
|---|---|---|---|---|---|---|
| | | | 10 MIN | 20 MIN | 30 MIN | 40 MIN |
| 0 | 11 | 0.00 ± 0.00 | 0.30 ± 0.16 | 0.93 ± 0.21 | 1.84 ± 0.19 | 2.10 ± 0.24 |
| 5 | 12 | 0.01 ± 0.01 | 0.31 ± 0.11 | 0.78 ± 0.23 | 1.47 ± 0.20 | 1.46 ± 0.19* |
| 10 | 11 | 0.00 ± 0.00 | 0.42 ± 0.17 | 0.33 ± 0.16* | 1.02 ± 0.27* | 1.05 ± 0.19* |
| 20 | 12 | 0.00 ± 0.00 | 0.48 ± 0.18 | 0.57 ± 0.14 | 0.78 ± 0.18* | 1.02 ± 0.24* |
| 40 | 12 | 0.00 ± 0.00 | 0.12 ± 0.05 | 0.10 ± 0.04* | 0.09 ± 0.06* | 0.12 ± 0.06* |

*= Significant difference from vehicle (ANOVA corrected for multiple comparisons $p \leq 0.05$.
The term ANOVA stands for Analysis of Variance.

These results support and confirm the hypothesized anti-neuropathic pain activity of the compound.

Data reported here support and give the necessary scientific basis for the activity observed earlier in the writhing test and the mouse formalin test. The former data being limited due to the fact that the writhing test is considered a very unspecific test with some tonic chemically-induced nociceptive aspects that usually gives positive results for all psychoactive drug muscle relaxants etc. therefore not being specific enough to claim specific activity. In addition, the former results obtained in the mouse formalin test, lacks clear evidence of dose relationship and therefore specificity of the observed effects for harkoseride. Furthermore, the only and highest dose giving significant effects in the first investigation already was found to cause clear behavioral side effects. Therefore, these drugs include changes in behavior, these drug-related changes cannot be claimed as antinociceptive any longer.

Therefore, only the newly reported data provided here can be considered an in vivo proven antinociceptive effect of harkoseride, with dose dependency serving as measure of specificity and improvement of antinociceptive behavior as being unrelated to toxic effects.

EXAMPLE 2

Chronic Constriction Injury (CCI, Bennett-model)

The effectiveness of harkoseride in reducing spontaneous chronic pain, mechanical allodynia, and thermal hyperalgesia was tested using the chronic constriction injury (CCI) model of peripheral neuropathy, one of the best characterised in vivo animal models used to study chronic pain due to peripheral nerve injury. In this model, loose ligatures are placed around the sciatic nerve, which produces axonal swelling and a partial deafferentation manifested as a significant but incomplete loss of axons in the distal portion of the peripheral nerve. One of the prominent behaviours seen following sciatic nerve ligation is the appearance of hind paw guarding, thought to be an indication of an ongoing spontaneous chronic pain. Support for this idea is derived from reports of increased spinal cord neural activity, and increased spontaneous neuronal discharge in spinothalamic tract neurons and in the ventrobasal thalamus in the absence of overt peripheral stimulation. In addition to the appearance of spontaneous pain behaviours, several abnormalities in stimulus evoked pain occur as a result of CCI, including thermal hyperalgesia and mechanical allodynia. The development of these abnormal stimulus-evoked pains has also been reported as occurring in areas outside the territory of the damaged nerve, areas innervated by uninjured nerves.

Behavioural tests for spontaneous pain, thermal hyperalgesia, and mechanical allodynia were conducted to evaluate different components of neuropathic pain. Baseline data for each test was collected prior to any experimental procedure; in addition, all animals were tested for the development of chronic pain behaviours 13-25 days after CCI surgery 1 day prior to the day of vehicle (0.04 ml sterile water/10 g body weight) or drug administration and after vehicle/drug administration. The sequence of the tests was (1) spontaneous pain-related behaviour (2) mechanical allodynia, (3) thermal hyperalgesia in order to minimise the influence of one test on the result of the next. The testing procedures and results are presented separately for each aspect of chronic pain. Either 0 (vehicle, 0.04 ml/10 g body weight), 5, 10, 20 or 40 mg/kg of SPM 927 (n=7-23/group) was administered i.p. 15 minutes before the first behavioural test.

Spontaneous pain (ongoing pain without an apparent external stimulus) of the ligated paw was assessed for 5 min following a 10 min acclimation period by use of a rating score (weighted behaviour score scaled 0-5).

Harkoseride did not change the level of spontaneous pain induced by unilateral chronic constriction injury as shown in table 2 (weighted pain scores±SEM).

TABLE 2

Spontaneous nociception, CCI model, rat

| Dose [mg/kg] | No. of Animals | Baseline | Post-op | Post-op + Drug |
|---|---|---|---|---|
| 0 | 23 | 0 ± 0 | 1.4 ± 0.15 | 1.2 ± 0.14 |
| 5 | 9 | 0 ± 0 | 2.0 ± 0.10 | 1.8 ± 0.18 |
| 10 | 20 | 0.0019 ± 0.0019 | 1.5 ± 0.10 | 1.5 ± 0.11 |
| 20 | 8 | 0 ± 0 | 1.1 ± 0.17 | 0.9 ± 0.14 |
| 40 | 10 | 0.0004 ± 0.0004 | 1.3 ± 0.12 | 0.8 ± 0.28 |

Thermal hyperalgesia was assessed by means of withdrawal latency in response to radiant heat applied to the subplantar surface of the ligated rat hind paw. As compared to the baseline latency(s), a significant decrease in the (postoperative) latency of foot withdrawal in response to the thermal stimulus was interpreted as indicating the presence of thermal hyperalgesia following chronic constriction injury.

Harkoseride dose dependently reduced chronic constriction injury-induced thermal hyperalgesia as shown in table 3 [latencies(s)±SEM]. Significant effects were observed only at the highest doses tested (20 and 40 mg/kg i.p.) with the maximum effect seen already at 20 mg/kg i.p.

TABLE 3

Thermal hyperalgesia, CCI model, rat

| Dose [mg/kg] | No. of Animals | Baseline | Post-op | Post-op + Drug |
|---|---|---|---|---|
| 0 | 13 | 9.8 ± 0.74 | 7.0 ± 0.29 | 7.3 ± 0.43 |
| 5 | 7 | 10.5 ± 0.68 | 8.1 ± 0.59 | 9.2 ± 0.98 |
| 10 | 7 | 9.2 ± 0.68 | 7.1 ± 0.60 | 8.1 ± 0.59 |
| 20 | 8 | 10.0 ± 0.70 | 7.0 ± 0.56 | 9.7 ± 0.96* |
| 40 | 8 | 8.3 ± 0.57 | 7.4 ± 0.48 | 10.2 ± 0.75* |

*= Significant difference from vehicle (ANOVA corrected for multiple comparisons p $\leq$ 0.05.

Mechanical sensitivity and allodynia of the ligated rat hind paw was quantified by brisk foot withdrawal in response to normally innocuous mechanical stimuli as described previously. Responsiveness to mechanical stimuli was tested with a calibrated electronic Von Frey pressure algometer connected to an online computerised data collection system. A significant decrease in the post operative compared to baseline pressure (g/mm$^2$) necessary to elicit a brisk foot withdrawal in response to this mechanical stimulus is interpreted as mechanical allodynia.

Harkoseride dose dependently reduced the intensity of mechanical allodynia induced by unilateral nerve ligation as shown in table 4 [pressure (g/mm$^2$)±SEM]. Regression analysis showed a positive linear correlation between the dose of Harkoseride and the increase in the amount of force required to produce foot withdrawal

TABLE 4

Mechanical allodynia, CCI model, rat

| Dose [mg/kg] | No. of Animals | Baseline | Post-op | Post-op + Drug |
|---|---|---|---|---|
| 0 | 20 | 41.6 ± 2.20 | 18.8 ± 2.09 | 20.2 ± 1.90 |
| 5 | 11 | 53.6 ± 3.35 | 16.4 ± 2.56 | 21.8 ± 2.34 |
| 10 | 17 | 42.9 ± 2.55 | 21.2 ± 2.13 | 29.2 ± 2.85* |
| 20 | 8 | 46.1 ± 2.62 | 24.7 ± 2.78 | 39.6 ± 3.62* |
| 40 | 9 | 48.4 ± 3.84 | 23.9 ± 2.23 | 43.0 ± 5.48* |

*= Significant difference from vehicle (ANOVA corrected for multiple comparisons, p $\leq$ 0.05).

These results support and confirm the hypothesised anti-allodynia efficacy of Harkoseride. Furthermore this effect is additionally related to neuropathic pain and therefore supports the potential clinical use of the compound by mimicking the clinical situation of symptom related treatment as close as possible.

Further proof of specificity of the anti-allodynia effect of harkoseride was given by negative results in the tail flick test excluding typical opioid-like analgesia of the compound. The former data obtained in mice could be repeated and confirmed in a second species, the rat, by additional means of more appropriate choice of the doses tested:

EXAMPLE 3

Tail Flick Test, Rat

Harkoseride was additionally tested for potential activity in acute spinal thermal nociception using the tail flick test. In this model of acute thermal spinal/reflex hyperalgesia radiant heat is applied to the animal's tail approximately 2 cm from the tip and time latency for withdrawal reaction is automatically assessed by an algometer, a defined maximal stimulus time prevents tissue damage. This test is widely used as an assay for the anti-nociceptive efficacy of pharmacological agents and is highly predictive of acute analgesic efficacy in humans. Usually pure analgesics of the opioid type are most active; neither adjuvants like amitryptiline nor anti-epileptics nor NSAIDs (non-steroidal anti-inflammatory drugs) are active.

Results for 20 and 40 mg/kg harkoseride i.p are shown in table 5 [percent anti-nociception, calculated as [{(post-drug latency)−(pre-drug-latency)}/{(max. latency)−(pre-drug latency)}×100]±SEM, n=12/group]. A baseline or pre-drug tail-flick latency was determined by averaging 5 consecutive measurements taken 2 minutes apart. Vehicle (sterile water 0.04 ml/10 g body weight) or harkoseride were then administered and tail flick latencies recorded at 10-minute intervals for the next 60 minutes. Even at doses giving maximum effect in the rat formalin test (see above), harkoseride had little or no effect on the latency of the tail flick reflex.

TABLE 5

Acute thermal hyperalgesia, tail flick, rat

| Time after SPM 927[min] | Anti-nociceptive effect [%] of different doses [mg/kg] of i.p. Harkoseride | | |
|---|---|---|---|
| | 0 | 20 | 40 |
| 10 | −2.1 ± 3.08 | 5.0 ± 3.94 | −1.6 ± 12.82 |
| 20 | −0.5 ± 3.19 | 9.7 ± 7.51 | −4.3 ± 14.04 |
| 30 | 4.4 ± 4.71 | 9.7 ± 2.37 | −2.3 ± 9.14 |
| 40 | 10.4 ± 5.91 | 1.7 ± 7.42 | −4.4 ± 11.44 |
| 50 | 7.6 ± 4.58 | 5.4 ± 4.12 | 0.3 ± 15.50 |
| 60 | 7.4 ± 6.07 | 8.1 ± 5.20 | −5.5 ± 14.11 |

Therefore no anti-nociceptive effect of harkoseride was detectable in the tail-flick test, this supports the hypothesised profile of harkoseride with higly specific anti-allodynia properties and not being active in conditions of acute pain.

EXAMPLE 4

The Anti-nociceptive Activity of Harkoseride in Comparison with Gabapentin

In the following explained study the used harkoseride is hereinafter abbreviated as SPM 927 and gabapentin is hereinafter abbreviated as GBP.

Objective:

The major aim of this study was to assess the anti-nociceptive activity of SPM 927 and gabapentin (GBP) in rodent models for inflammatory pain and to compare the in vivo effects of each drug with each other.

Methods:

Carrageenan-induced mechanical hvderalcesia in rats was induced by subplantar injection of a 0.1 ml of a 2% carrageenan suspension and measured 3 h afterwards by the paw pressure (Randall-Sellito) test.

Subchronic inflammatory nocicoetion in mice was induced by the subplantar injection of formalin (0.02 ml of a 5% solution). Nociceptive behaviour (paw licking) was measured and quantified between 0 and 5 min (acute pain) and between 20 and 30 min (subchronic inflammatory pain) after formalin.

Drugs and experimental design: SPM 927 and GBP were suspended in 1% methylcellulose and administered i.p. at doses of 10 mg/kg, 20 mg/kg and 40 mg/kg. Pre-treatment time was 30 min before pain measurement. One group of animals served as controls and consequently received an injection of solvent (10 ml/kg) and another group of animals received a reference compound (Carrageenan test: 10 mg/kg indomethacin; Formalin test: 10 mg/kg morphine). Each compound was tested in a separate experiment and each experiment included a control and a reference group. 10 rats per group were used in the Carrageenan test and 6 mice per group in the formalin test.

Results:

Carrageenan-induced mechanical hyieralgesia in rats: Results are summarized in the following table 6.

TABLE 6

| | VEHICLE non-inflamed paw | VEHICLE inflamed paw | SPM 927 [10] | SPM 927 [20] | SPM 927 [40] | Indomethacin [10] |
|---|---|---|---|---|---|---|
| nociceptive threshold | 330 ± 16 | 164 ± 15[a] | 324 ± 15[b] | 426 ± 24[b] | 444 ± 13[b] | 384 ± 11[b] |

| | VEHICLE non-inflamed paw | VEHICLE inflamed paw | GBP [10] | GBP [20] | GBP [40] | Indomethacin [10] |
|---|---|---|---|---|---|---|
| nociceptive threshold | 396 ± 15 | 204 ± 10[a] | 254 ± 39 | 296 ± 31 | 282 ± 33 | 370 ± 15[b] |

[a] indicates a significant difference in comparison with the non-inflamed paw (p < 0.05; Student's t-test)

[b] indicates a significant difference in comparison with the vehicle treated group (p < 0.05; Dunnett's test)

In all three experiments significant mechanical hyperalgesia developed as showin by significant differences in the nociceptive threshold in the inflamed as compared to the non-inflamed paw.

All doses of SPM 927 resulted in a full reversal of Carrageenan-induced mechanical hyperalgesia.

The antinociceptive of SPM 927 was comparable to that of the reference compound Indomethacin.

GBP had no significant effect on Carrageenan induced mechanical hyperalgesia at the doses tested.

Subchronic Inflammatory nociception in mice (formalin test): Results are summarized in the following table 7.

TABLE 7

| | Phase | VEHICLE | SPM 927 [10] | SPM 927 [20] | SPM 927 [40] | Morphine [10] |
|---|---|---|---|---|---|---|
| nociceptive threshold [s] | early | 84 ± 16 | 67 ± 15 | 69 ± 8 | 8 ± 8$^a$ | 6 ± 3$^a$ |
| | late | 119 ± 18 | 58 ± 16$^a$ | 128 ± 16 | 17 ± 17$^a$ | 10 ± 8$^a$ |

| | | VEHICLE | GBP [10] | GBP [20] | GBP [40] | Morphine [10] |
|---|---|---|---|---|---|---|
| nociceptive threshold [s] | early | 106 ± 15 | 98 ± 20 | 102 ± 17 | 72 ± 10 | 8 ± 6$^a$ |
| | late | 111 ± 24 | 133 ± 30 | 118 ± 13 | 73 ± 13 | 0 ± 0$^a$ |

$^a$indicates a significant difference in comparison with the vehicle treated group (p < 0.05; Dunnett's test)

A clear nociceptive response was induced by formalin. SPM-927 dose dependently suppressed the nociceptive response. The efficacy of SPM 927 was similar to that of morphine i.e. a near complete reversal of the formalin-induced nociception. GBP slightly but not significantly inhibited the nociceptive response induced by formalin

EXAMPLE 5

The following Tables 8 and 9 show the effects of harkoseride (hereinafter referred to as SPM 927), carbamazepine, levetiracetam, gabapentin and morphine in the neuropathic pain (CHUNG) test in the rat. Eight (8) rats per group were used.

Table 8 shows the examined effects by tactile stimulation on lesioned paw.

Table 9 shows the examined effects by thermal stimulation on lesioned paw.

In general, all compounds showed more pronounced effects on tactile nociceptive stimulation than on thermal nociceptive stimulation, and SPM 927 was minimum comparable, but usually more potent than the reference compounds.

TABLE 8

EFFECTS OF SPM 927, CARBAMAZEPINE,
LEVETIRACETAM GABAPENTIN AND MORPHINE
IN THE NEUROPATHIC PAIN (CHUNG) TEST
IN THE RAT
(8 RATS PER GROUP)
TACTILE STIMULATION
(lesioned paw)

| TREATMENT (mg/kg) i.p. −30 min | FORCE INDUCING PAW-WITHDRAWAL (g) | | |
|---|---|---|---|
| | mean ± s.e.m. | p value | % change |
| Sham control | 63.3 ± 4.5 | — | — |
| Lesioned control | 17.4 ± 2.2 *** (a) | 0.000 | −73% (a) |
| SPM 927 (8) | 27.2 ± 4.9 NS (b) | 0.094 | +56% (b) |
| SPM 927 (16) | 24.4 ± 3.0 NS (b) | 0.086 | +40% (b) |
| SPM 927 (32) | 37.6 ± 6.1 ** (b) | 0.008 | +116% (b) |
| Carbamazepine (16) | 21.0 ± 2.3 NS (b) | 0.275 | +21% (b) |
| Carbamazepine (32) | 38.4 ± 8.1 * (b) | 0.026 | +121% (b) |
| Carbamazepine (64) | 39.2 ± 9.1 * (b) | 0.036 | +125% (b) |
| Levetiracetam (16) | 23.0 ± 4.0 NS (b) | 0.243 | +32% (b) |
| Levetiracetam (32) | 25.0 ± 5.2 NS (b) | 0.199 | +44% (b) |
| Levetiracetam (64) | 19.8 ± 4.1 NS (b) | 0.612 | +14% (b) |
| Gabapentin (32) | 17.2 ± 3.0 NS (b) | 0.959 | −1% (b) |
| Gabapentin (64) | 23.5 ± 4.2 NS (b) | 0.219 | +35% (b) |
| Gabapentin (128) | 33.6 ± 6.7 * (b) | 0.038 | +93% (b) |
| Morphine (16) | 45.9 ± 8.8 ** (b) | 0.007 | +164% (b) |

Student's t-test (non-paired):
NS = Not Significant;
* = p < 0.05;
** = p < 0.01;
*** = p < 0.001
(a) compared with sham control
(b) compared with lesioned control

TABLE 9

EFFECTS OF SPM 927, CARBAMAZEPINE,
LEVETIRACETAM GABAPENTIN AND MORPHINE
IN THE NEUROPATHIC PAIN (CHUNG) TEST
IN THE RAT
(8 RATS PER GROUP)
THERMAL STIMULATION
(lesioned paw)

| TREATMENT (mg/kg) i.p. −30 min | PAW-WITHDRAWAL LATENCY (sec) | | |
|---|---|---|---|
| | mean ± s.e.m. | p value | % change |
| Sham control | 40.6 ± 2.2 | — | — |
| Lesioned control | 16.3 ± 4.4 *** (a) | 0.000 | −60% (a) |
| SPM 927 (8) | 26.1 ± 5.4 NS (b) | 0.180 | +60% (b) |
| SPM 927 (16) | 16.8 ± 4.5 NS (b) | 0.933 | +3% (b) |
| SPM 927 (32) | 21.1 ± 5.6 NS (b) | 0.512 | +29% (b) |
| Carbamazepine (16) | 35.6 ± 4.1 ** (b) | 0.006 | +118% (b) |
| Carbamazepine (32) | 22.7 ± 4.3 NS (b) | 0.315 | +39% (b) |
| Carbamazepine (64) | 28.8 ± 6.9 NS (b) | 0.147 | +77% (b) |
| Levetiracetam (16) | 19.0 ± 3.6 NS (b) | 0.641 | +17% (b) |
| Levetiracetam (32) | 17.1 ± 2.9 NS (b) | 0.882 | +5% (b) |
| Levetiracetam (64) | 26.6 ± 6.0 NS (b) | 0.187 | +63% (b) |
| Gabapentin (32) | 19.3 ± 3.6 NS (b) | 0.611 | +18% (b) |

TABLE 9-continued

EFFECTS OF SPM 927, CARBAMAZEPINE,
LEVETIRACETAM GABAPENTIN AND MORPHINE
IN THE NEUROPATHIC PAIN (CHUNG) TEST
IN THE RAT
(8 RATS PER GROUP)
THERMAL STIMULATION
(lesioned paw)

| TREATMENT | PAW-WITHDRAWAL LATENCY (sec) | | |
|---|---|---|---|
| (mg/kg) i.p. −30 min | mean ± s.e.m. | p value | % change |
| Gabapentin (64) | 28.5 ± 5.4 NS (b) | 0.101 | +75% (b) |
| Gabapentin (128) | 27.1 ± 5.2 NS (b) | 0.135 | +66% (b) |
| Morphine (16) | 42.4 ± 1.9 *** (b) | 0.000 | +160% (b) |

Student's t-test (non-paired):
NS = Not Significant;
** = p < 0.01;
*** = p < 0.001
(a) compared with sham control
(b) compared with lesioned control

The invention claimed is:

1. A method of treating allodynia in a subject suffering therefrom, comprising administering to the subject an effective amount of a compound of formula (I):

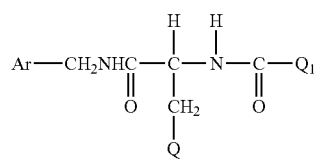

wherein:
Ar is phenyl which is unsubstituted or substituted with at least one halo group;
Q is lower alkoxy containing 1-3 carbon atoms; and
$Q_1$ is methyl;
or a pharmaceutically acceptable salt thereof; wherein the allodynia is not related to neuropathic pain.

2. The method of claim 1 wherein the compound or pharmaceutically acceptable salt thereof is in the R configuration.

3. The method of claim 1 wherein, in the compound of formula (I), Ar is unsubstituted phenyl.

4. The method of claim 1 wherein, in the compound of formula (I), halo is fluoro.

5. The method of claim 1 wherein the compound of formula (I) is (R)-2-acetamido-N-benzyl-3-methoxypropionamide or a pharmaceutically acceptable salt thereof.

6. The method of claim 1 wherein the subject is suffering from chronic pain.

7. The method of claim 1 wherein the subject is suffering from phantom pain.

8. The method of claim 1, wherein the compound of formula (I) or a pharmaceutically acceptable salt thereof is administered in a dosage amount of about 1 mg/day to about 600 mg/day.

9. The method of claim 1, wherein the compound of formula (I) or a pharmaceutically acceptable salt thereof is administered in a dosage amount of about 1 mg/day to about 300 mg/day.

10. The method of claim 8, wherein the compound of formula (I) is administered in an oral dosage amount of about 1 mg/day to about 600 mg/day.

* * * * *

UNITED STATES PATENT AND TRADEMARK OFFICE
CERTIFICATE OF CORRECTION

| | |
|---|---|
| PATENT NO. | : 7,875,652 B2 |
| APPLICATION NO. | : 10/466295 |
| DATED | : January 25, 2011 |
| INVENTOR(S) | : N. Selve |

It is certified that error appears in the above-identified patent and that said Letters Patent is hereby corrected as shown below:

Column 1, line 63, "Included" should be changed to --included--.

Column 3, line 58, "Independent" should be changed to --independent--.

Column 4, line 26, "well-knwon" should be changed to --well-known--.

Column 5, line 6, "efficay" should be changed to --efficacy--.

Column 7, line 45, "latencies(s)" should be changed to --latency(s)--.

Column 8, line 11, "withdrawal" should be changed to --withdrawal.--.

Column 10, line 5, "hvderalcesia" should be changed to --hyperalgesia--.

Column 10, line 9, "nocicoetion" should be changed to --nociception--.

Column 10, line 30, "hyieralgesia" should be changed to --hyperalgesia--.

Column 10, line 56, "showin" should be changed to --shown--.

Column 11, line 21, "formalin" should be changed to --formalin.--.

Signed and Sealed this
Twenty-seventh Day of September, 2011

David J. Kappos
*Director of the United States Patent and Trademark Office*